United States Patent [19]

Stautzenberger

[11] 3,931,249

[45] Jan. 6, 1976

[54] EPOXIDATION USING PHTHALOCYANINE CATALYSTS

[75] Inventor: Adin Lee Stautzenberger, Corpus Christi, Tex.

[73] Assignee: Celanese Corporation, New York, N.Y.

[22] Filed: Feb. 13, 1974

[21] Appl. No.: 442,273

Related U.S. Application Data

[63] Continuation-in-part of Ser. No. 105,134, Jan. 8, 1971, abandoned, which is a continuation of Ser. No. 746,289, July 22, 1968, abandoned.

[52] U.S. Cl............................................ 260/348.5 L
[51] Int. Cl.² ........................................ C07D 301/20
[58] Field of Search ............................. 260/348.5 L

[56] References Cited
UNITED STATES PATENTS

| | | | |
|---|---|---|---|
| 3,333,010 | 7/1967 | Urbanek | 260/617 |
| 3,350,422 | 10/1967 | Kollar | 260/348.5 L |
| 3,351,635 | 11/1967 | Kollar | 260/348.5 L |
| 3,391,214 | 7/1968 | Fetterly | 260/681 |
| 3,505,360 | 4/1970 | Allison | 260/348.5 L |

OTHER PUBLICATIONS

N. Indictor et al., Jour. Org. Chemistry, Vol. 30, pp. 2074–2075.

*Primary Examiner*—Norma S. Milestone
*Attorney, Agent, or Firm*—Stewart N. Rice; Ralph M. Pritchett

[57] ABSTRACT

A process for the epoxidation of ethylenically unsaturated compounds with organic hydroperoxides using metal-free phthalocyanines or metal phthalocyanines as catalysts. Suitable metals include those of the metals Ni, Cu, Ag, Ti, V, Zr, Mo, Re, or U.

6 Claims, No Drawings

EPOXIDATION USING PHTHALOCYANINE CATALYSTS

BACKGROUND OF THE INVENTION

This is a continuation-in-part of copending patent application Ser. No. 105,134, filed Jan. 8, 1971 and now abandoned, which in turn is a continuation of application Ser. No. 746,289, filed July 22, 1968, and now abandoned.

The present invention relates to the epoxidation of ethylenically unsaturated compounds.

It is well known that ethylenically unsaturated compounds, i.e., those having at least one aliphatic double bond ($>C=C<$), may undergo a liquid phase reaction with organic hydroperoxides in the presence of a catalyst so as to form oxirane epoxides according to the following reaction:

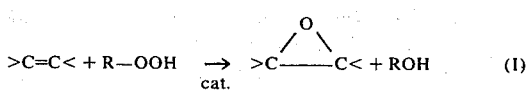

For example see Belgian Pat. No. 665,082 which discloses the epoxidation of unsaturated compounds using catalysts of compounds of Mo, W, V, Se, Ti, Cr, Nb, Zr, Te, Ta, Re or U together with a basic compound. Also see Indicator, "Metal Acetylacetonate Catalyzed Epoxidation of Olefins with t-Butyl Hydroperoxide," *Journal of Organic Chemistry*, Volume 30, page 2074, wherein the use of acetylacetonates of Cr, V, VO, MoO$_2$, Co, Cu, and Mn are reported as epoxidation catalysts using a t-butyl hydroperoxide epoxidizing agent. Even though these and other catalysts are effective in producing oxirane epoxides from ethylenically unsaturated compounds and organic hydroperoxides, research has continued directed toward new and efficient catalysts for this reaction.

SUMMARY

It is thus an object of the present invention to provide a process for the reaction of an organic hydroperoxide and an ethylenically unsaturated compound so as to introduce an oxirane oxygen at the site of an ethylenic double bond in the ethylenically unsaturated compound. It is also an object of the present invention to provide a catalyst for promoting the epoxidation of ethylenically unsaturated compounds with organic hydroperoxides.

These and other objects are accomplished by the present invention which in one of its embodiments is an improvement in a process wherein an ethylenically unsaturated compound is catalytically reacted in the liquid phase with an organic hydroperoxide so as to introduce an oxirane oxygen at the site of an ethylenic double bond in said ethylenically unsaturated compound, which improvement comprises using a metal-free phthalocyanine compound or a metal salt of said phthalocyanine compound as a catalyst, said metal being nickel, copper, silver, titanium, vanadium, zirconium, molybdenum, rhenium, or uranium. That nickel phthalcyanine is effective in this improved process is especially surprising, since nickel acetylacetonate is not effective whereas metal moieties that are good epoxidation catalysts are normally effective as the acetylacetonates.

DESCRIPTION OF THE PREFERRED EMBODIMENTS

The ethylenically unsaturated compounds which may be oxidized in accordance with the present invention are preferably hydrocarbons free of acetylenic unsaturation and may have one or a plurality of ethylenic double bonds. These compounds may be aromatic or non-aromatic and may be either monomers or polymers. Examples of ethylenically unsaturated hydrocarbons which may be epoxidized in accordance with the present invention include propylene, butenes, pentenes, hexenes, heptenes, octenes, decenes, dodecenes, octadecenes, butadiene, isoprene, pentadienes, hexadienes, heptadienes, octadienes, decadienes, dodecadienes, octadecadienes, styrene, divinylbenzenes, dihydronaphthalenes, indene, stilbene, 1-phenyl-1-propene, 1,1-diphenylene, cyclopentenes, cyclohexense, cyclopentadiene, dicyclopentadiene bicycloheptadiene, vinylcyclohexenes, alkyl-substituted cycloalkenes, alkyl-substituted cycloalkadienes, aryl-substituted alkadienes, aryl-substituted cyclopentenes, unsaturated macromolecules such as butadiene polymer and copolymers, and the like. Although the present process is not limited thereto, best results are generally obtained when epoxidizing non-aromatic hydrocarbons of 3–20 carbon atoms, the only unsaturation being a single ethylenic double bond, for example, propylene, cyclohexene, vinyl cyclohexane, etc.

The catalysts which may be used in the present process are metalfree phthalocyanine compounds and certain metal phthalocyanine compounds. These phthalocyanine compounds which may be utilized as catalysts in the present invention are generally insoluble compounds which may be made by methods well described in the chemical literature and well summarized in Moser et al., *Phthalocyanine Compounds*, A.C.S. Monograph No. 157, Reinhold Publishing Corporation, 1963. The fact that the catalysts of the present invention are generally insoluble makes them preferable to the prior art catalysts mentioned above since those catalysts are soluble and thus present a problem of separating them from the reaction products. For another discussion of phthalocyanine compounds attention is directed to Lever, A.B.P., *Advances in Inorganic Chemistry and Radiochemistry*, Academic Press, Volume 7, 1965, pages 27–114.

In general the metal-free phthalocyanine compounds which may be used in the present invention are phthalocyanine compounds of the structural formula

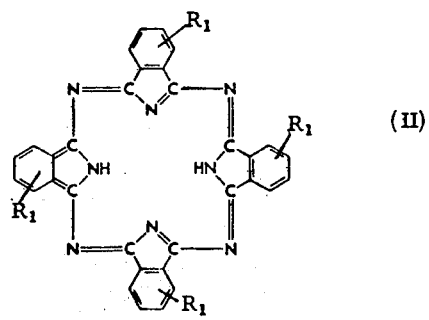

wherein R$_1$ is hydrogen or a hydrocarbon radical free of ethylenic and acetylenic unsaturation, each R$_1$ being alike or different and preferably being of 1 to 8 carbon atoms when $R_1$ is a hydrocarbon radical. Thus $R_1$ could in addition to hydrogen be such radicals as methyl, ethyl, pentyl, benzyl, phenyl, cyclohexyl, and the like. When each $R_1$ of Formula (II) is hydrogen, the compound would be phthalocyanine itself which is the preferred non-metal phthalocyanine compound for use in the present process. Other metal-free phthalocyanines which may be used as catalysts are those of Formula (II) which have halo or sulfo, i.e. — $SO_3H$, substituents. Of the halo-substituted phthalocyanines those of chlorine and bromine are preferred.

The metal phthalocyanine compounds which may be utilized as catalysts in the present invention are in general the metal derivatives of those phthalocyanine compounds mentioned above which themselves are effective catalysts. These metal phthalocyanines are formed by replacing the two hydrogen atoms in the center of the molecule of Formula (II) with a metal which may be nickel, copper, silver, titanium, vanadium, zirconium, molybdenum, rhenium, or uranium. The metal phthalocyanines are generally considered to be salts since phthalocyanine itself is considered to be an extremely weak dibasic acid. Depending on the valence of the metal which replaces the two hydrogen atoms there may also be one or more oxygen atoms attached to the metal and therefore the metal phthalocyanines useful as catalysts in the present invention usually are of the general formula

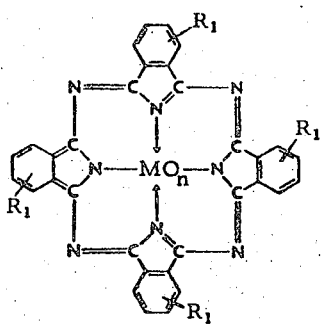

wherein $R_1$ is as described above, wherein $n$ is a number of 0–6 wherein M represents a metal. The halo and/or sulfo-substituted derivatives of the metal phthalocyanines of Formula III are also effective catalysts in the present process. Illustrative of specific metal salts of phthalocyanine compounds which may be used as catalysts in the present invention are nickel phthalocyanine

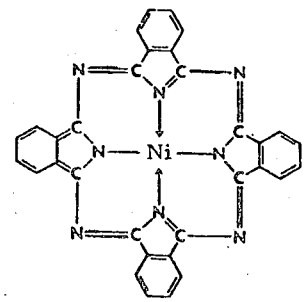

and vanadyl phthalocyanine

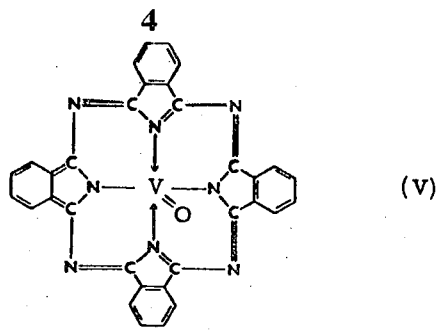

Other useful phthalocyanine compounds include copper tetra-3-chlorophthalocyanine, tetramethyl phthalocyanine, nickel phthalocyanine di-3sulfonic acid, zirconium monochlorophthalocyanine $[C_{32}H_{15}N_8Cl.Zr(OH)_2.2H_2O]$, copper tetra-4-nitrophthalocyanine, titanium monochlorophthalocyanine, vanadyl monochlorophthalocyanine, silver phthalocyanine, molybdenum phthalocyanine, uranyl phthalocyanine, uranyl phthalocyanine sulfonic acid, phthalocyanine tetrasulfonic acid, rhenium phthalocyanine, naphthalocyanine, copper chloro-1,2-naphthalocyanine, bis(chloromethyl)-phthalocyanine, bromomethyl phthalocyanine, tetrachloro phthalocyanine, tetraphenyl phthalocyanine, tetranitro phthalocyanine, tris(hydroxybenzyl) phthalocyanine. Of the various metal phthalocyanines which may be utilized, best results are obtained when the metal is nickel, vanadium or molybdenum while the preferred phthalocyanine compound from which metal phthalocyanine is formed is phthalocyanine itself.

In using the phthalocyanine compounds as catalysts in the present process they may advantageously be present in the mixed reactants at the start of a batch-type reaction in amounts so as to provide from about $10^{-6}$ to 0.1 moles per mole of ethylenic double bond provided by the ethylenically unsaturated compound being oxidized. Preferably the phthalocyanine compound catalysts are present in amounts of from about $10^{-5}$ to $10^{-3}$ moles per mole of ethylenic double bond in the ethylenically unsaturated compound being epoxidized. More broadly stated, whether the reaction technique be batchwise or continuous, a concentration of phthalocyanine compound of at least about $10^{-6}$ molar in the liquid contained in the reaction zone is recommended, more preferably $10^{-6}$ to 0.1 molar and most preferably $10^{-5}$ to $10^{-3}$ molar.

The epoxidation reaction can be conducted at temperatures which generally vary from 50 to about 200°C although temperatures of from about 80° to about 150°C are preferred. The operative pressure should be sufficient to maintain a liquid phase epoxidation reaction medium. Usually these pressures will be from about atmospheric, or slightly above, to about 5,000 psig, depending of course on the particular reactants being employed and the temperature at which the reaction is being conducted. Most often the pressure will vary from about 30 to 1,000 psig.

Practically any organic hydroperoxide may be utilized in the present process. The term "organic hydroperoxide" as used herein is used in its generally accepted sense and is not intended to include peracids such as peracetic acid and the like. In general the organic hydroperoxides useful in the present invention are of the formula $R_2$-OOH wherein $R_2$ is a hydrocarbon radical, halo-substituted hydrocarbon radical, hydroxyl substituted hydrocarbon radical, or nitro-substituted hydrocarbon radical. The radical $R_2$ preferably contains from about 3–20 atoms and is preferably free of ethylenic and acetylenic unsaturation. Of the various organic hydroperoxides that may be used the tertiary hydroperoxides are especially useful. Specific examples of suitable organic hydroperoxides include chlorotertiary butyl hydroperoxide, p-cymene hydroperoxide, para-methane hydroperoxide, tertiary amyl hydroperoxide, lauryl hydroperoxide, benzyl hydroperoxide, cyclohexyl hydroperoxide, cyclohexene hydroperoxide, bromo-tertiary butyl hydroperoxide, eicosyl hydroperoxide, 1,1-dichloromethylpropyl hydroperoxide, tertiary butyl hydroperoxide, isopropyl hydroperoxide, sec-butyl hydroperoxide, alpha, alpha-dimethylbenzyl hydroperoxide, chloro-tertiary butyl hydroperoxide, 1-chloromethyl-1-bromomethylpropyl hydroperoxide, 1-methylcyclohexyl hydroperoxide, cyclohexanol hydroperoxide, alpha, alpha-dimethyl-p-nitrobenzyl hydroperoxide, 2-chloro-1-hydroxycyclohexyl hydroperoxide, 2-hydroxyethyl hydroperoxide and alpha-methyl-p-nitrobenzyl hydroperoxide. It is apparent from Equation (I) that a molecule of organic hydroperoxide is consumed for each ethylenic double bond which is epoxidized; however, the hydroperoxide epoxidizing agent and the ethylenically unsaturated compound may be used in a wide variety of proportions. Generally the ethylenically unsaturated compound and organic hydroperoxide should be present in amounts such that there are from about 0.8 to 10 ethylenic double bonds which are to be epoxidized per molecule of organic hydroperoxide, preferably 1.0 to 2.0 ethylenic double bonds which are to be epoxidized per molecule of organic hydroperoxide.

The present invention may be carried out either continuously, intermittently or batchwise and the reactants may be added in any order. Stirring the reactants or some other form of agitation is not necessary, but does reduce the time required to complete the reaction by promoting intimate contact of the reactants.

The reaction may be carried out with or without a solvent but it is generally preferred to carry out the reaction in a solvent so as to facilitate the handling of reactants which either have high vapor pressure, requiring high process pressure to maintain a liquid phase, or else are of high viscosity such that a non-viscous solvent facilitates mixing and pumping. Taking propylene as an example of a feedstock with which a solvent might be used advantageously, it will be recognized that propylene has a comparatively high vapor pressure although this vapor pressure is low enough that, if desired, propylene can be epoxidized without a solvent by simply maintaining a reaction pressure sufficiently high that the propylene is kept in the liquid phase during the reaction. In other words, a reaction solvent facilitates handling but is not essential. Advantageously, however, the required reaction pressure is reduced by incorporating into the reaction feedstock an inert liquid which is miscible with propylene and which, at the reaction temperatures, is either liquid or has a vapor pressure not greatly exceeding atmospheric pressure. Any of a very large number of solvents is applicable, as explained hereinbelow, but with propylene it is particularly convenient to employ as solvent a hydrocarbon liquid which is free of unsaturation other than aromatic. (It will be recognized, of course, that one could, if desired, employ an ethylenically unsaturated hydrocarbon of the desired low vapor pressure as a reactive solvent, the result being formation of a mixture of the epoxides of this solvent hydrocarbon with propylene oxide, this mixture then being resolved, as by distillation, after conclusion of the reaction.) Generally speaking, however, propylene is advantageously epoxidized in the presence of inert hydrocarbons such as benzene, alkylbenzenes, and saturated aliphatic or alicyclic hydrocarbons having at least about 6 carbon atoms in the molecule, preferably from about 6 to about 12 carbon atoms. The proportion of propylene to solvent in the reaction mixture is not critical, although a relatively high proportion is to be preferred.

The particular solvent which is used in a given instance is not critical and suitable solvents include hydrocarbons (especially those which are free of unsaturation other than aromatic unsaturation), alcohols, ketones, ethers, and esters which are miscible with the olefinic feedstock. Some specific suitable solvents include benzene, toluene, xylenes, pentanes, hexane, cyclohexane, methanol, ethanol, propanol, tertiary butyl alcohol, isopropanol, ethylene glycol, acetone, methyl ethyl ketone, cyclohexanol, dimethyl ether, ethylene glycol monomethyl ether, dioxane, and ethylene glycol monoacetate. The solvents which are used may be either reactive or non-reactive. However, the non-reactive solvents are preferred because recovery of the reaction product from them is facilitated. By "non-reactive" is meant a solvent species which, under the reaction conditions, is inert toward hydroperoxides and epoxides.

Following the completion of the epoxidation reaction the seperation of the reaction product may be effected by conventional techniques such as distillation, fractionation, extraction, crystallization and the like. Normally the effluent from the reaction zone will comprise unreacted ethylenically unsaturated compounds, the epoxide product, insoluble catalyst, solvent for the ethylenic compound, if employed, and the like. A preferable procedure for separating the epoxide products from the reactor effluent is by filtering or centrifuging away the catalyst and then separating the unreacted ethylenically unsaturated compound, epoxide and solvent by distillation. The catalyst may be recycled and utilized again if desired.

The following examples are given to illustrate the present invention but are not to be taken in a limiting sense.

EXAMPLE I

Several runs were made in which cyclohexene was epoxidized with t-butyl hydroperoxide using various catalysts. In conducting each of the runs a glass flask fitted with a reflux condenser was charged with 190 millimoles of cyclohexene, 7.9 millimoles of t-butyl hydroperoxide and 0.02 millimoles of catalyst. The contents of the flask were then refluxed at 82°C for a time and then the reaction product analyzed to determine the amount of t-butyl hydroperoxide which had been converted as well as what percent of that which had been converted went to the epoxide. The results of the several runs are listed in Table I with the initials "Pc" in Table I standing for phthalocyanine.

TABLE I

| Run No. | Catalyst | Time, hr | Hydroperoxide Conversion, % | Efficiency to Epoxide, % |
|---|---|---|---|---|
| 1 | Ni Pc | 5 | 74 | 97.3 |
| 2 | Phthalocya- | 3 | 18 | 32 |

TABLE I-continued

| Run No. | Catalyst | Time, hr | Hydroperoxide Conversion, % | Efficiency to Epoxide, % |
|---|---|---|---|---|
| 3 | Cu Pc | 2.5 | 22 | 22 |
| 4 | Ag Pc | 3 | 24 | 27 |
| 5 | MoO Pc | 2 | 87 | 99 |
| 6 | VO Pc | 2 | 60 | 75 |
| 7[a] | Ni Pc | 2 | 56 | 68 |

[a] Cyclohexanol hydroperoxide used

EXAMPLE II

A glass flask fitted with a reflux condenser was charged with 50 millimoles of cyclohexene, 1.6 millimoles of cyclohexyl hydroperoxide, and 0.005 millimoles of a nickel phthalocyanine catalyst. After refluxing the contents of the flask at 82°C for about 19 hours, analysis showed that 99% of the cyclohexyl hydroperoxide had been converted with 99% of that converted going to the cyclohexene epoxide.

EXAMPLE III

A glass flask fitted with a reflux condenser was charged with 128 millimoles of octene-1, 7.9 millimoles of t-butyl hydroperoxide, and 0.02 millimoles of nickel phthalocyanine catalyst. The contents of the flask were then refluxed at 113°C for 100 minutes and then the contents analyzed. Analysis showed that 30% of the hydroperoxide had been converted with 88% of that converted going to 1,2-octene epoxide.

The embodiments of the invention in which an exclusive property or privilege is claimed are defined as follows:

1. In a process for the catalytic reaction of an organic hydroperoxide with an ethylenically unsaturated hydrocarbon of 3 to about 20 carbon atoms which is free of acetylenic unsaturation so as to introduce an oxirane oxygen at the site of an ethylenic double bond in said hydrocarbon, the improvement which comprises employing nickel phthalocyanine as catalyst for said reaction, the reaction being conducted in a reaction zone containing a liquid reaction medium consisting essentially of ethylenically-unsaturated hydrocarbon or mixtures of ethylenically-unsaturated hydrocarbon with an unreactive reaction solvent, together with said hydroperoxide and said catalyst, the reaction temperature being about 80° to 150°C, the reaction pressure being one which is high enough to keep said reaction medium in the liquid phase, and the concentration of nickel phthalocyanine in said reaction medium being at least about $10^{-6}$ molar.

2. The process of claim 1 wherein the hydrocarbon is an aliphatic or alicyclic hydrocarbon of 3 to about 20 carbon atoms.

3. The process of claim 1 wherein there are introduced into said reaction zone as reaction feedstocks about 0.8 to 10 ethylenic double bond moieties per mole of said organic hydroperoxide introduced thereinto.

4. The process of claim 3 wherein said organic hydroperoxide is of the formula $R_2$—OOH wherein $R_2$ is a hydrocarbon, halo-substituted hydrocarbon, hydroxyl-substituted hydrocarbon, or nitro-substituted hydrocarbon of 3 to about 20 carbon atoms.

5. The process of claim 4 wherein said organic hydroperoxide is of the formula $R_2$—OOH wherein $R_2$ is a hydrocarbon radical of 3 to about 20 carbon atoms free of ethylenic and acetylenic unsaturation.

6. The process of claim 5 wherein said ethylenically-unsaturated hydrocarbon is an aliphatic or alicyclic hydrocarbon of 3 to about 20 carbon atoms having in the molecule a single double bond.

* * * * *